United States Patent [19]

Yamamoto

[11] Patent Number: 5,987,720
[45] Date of Patent: Nov. 23, 1999

[54] PORTABLE TOMB FOR RESURRECTION FROM MUMMIFIED TISSUE DNA

[76] Inventor: William Shigeru Yamamoto, 3234 N. 5th St., Arlington, Va. 22201-1702

[21] Appl. No.: 08/889,190

[22] Filed: Jul. 8, 1997

[51] Int. Cl.⁶ .................................................. A61G 17/00
[52] U.S. Cl. ...................... 27/35; 27/1; 27/21.1; 422/40
[58] Field of Search .................................. 27/1, 35, 21.1; 52/103, 104; 40/124.5; 428/13; 422/1, 40; 435/1

[56] References Cited

U.S. PATENT DOCUMENTS

| | | |
|---|---|---|
| 397,379 | 2/1889 | Meyers . |
| 748,284 | 12/1903 | Karwowski . |
| 1,088,977 | 3/1914 | Fratarcangeli et al. . |
| 1,120,336 | 12/1914 | Schnee et al. . |
| 1,252,090 | 1/1918 | Clayton . |
| 2,106,261 | 1/1938 | Weidmann . |
| 2,124,143 | 7/1938 | Long ................................... 40/124.5 X |
| 3,408,712 | 11/1968 | Pauliukonis et al. . |
| 4,058,940 | 11/1977 | McBrayer . |
| 4,067,091 | 1/1978 | Backman . |
| 4,304,076 | 12/1981 | Splendora . |
| 4,337,109 | 6/1982 | Narita . |
| 4,455,772 | 6/1984 | Miller ..................................... 40/124.5 |
| 4,739,595 | 4/1988 | Yamagata . |
| 4,759,105 | 7/1988 | Buerosse ....................................... 27/1 |
| 5,014,472 | 5/1991 | Svensson . |
| 5,158,174 | 10/1992 | Hereford . |
| 5,255,170 | 10/1993 | Plamp . |
| 5,287,603 | 2/1994 | Schorman . |
| 5,349,727 | 9/1994 | Niebergall ..................................... 27/1 |
| 5,350,670 | 9/1994 | Yeh . |
| 5,379,499 | 1/1995 | Jackson . |
| 5,404,343 | 4/1995 | Boggio . |
| 5,405,606 | 4/1995 | Campbell et al. . |
| 5,564,816 | 10/1996 | Arcadia et al. . |
| 5,607,668 | 3/1997 | Campbell et al. . |
| 5,622,695 | 4/1997 | Campbell et al. . |
| 5,625,933 | 5/1997 | Neuberger et al. ...................... 27/35 X |
| 5,704,103 | 1/1998 | Crowley et al. .................... 40/124.5 X |
| 5,729,921 | 3/1998 | Rojas ......................................... 27/1 X |

OTHER PUBLICATIONS

Service, R.F. "Just How Old is That DNA Anyway?" Science vol. 272 p. 810 1996.
Grimaldi, D.A. "Captured in Amber" Scientific American Apr. 1996 pp. 84–91.
Casting Guide 82 pp. Copyright 1996 Castcraft, Box 17000 Memphis, TN 38187–0000.
Castolite (Brochure) 1996 The Castolite Company Woodstock, IL 60098.

*Primary Examiner*—Terry Lee Melius
*Assistant Examiner*—William L. Miller
*Attorney, Agent, or Firm*—Blank, Rome, Comisky & McCauley LLP

[57] ABSTRACT

A portable object prepared by casting a substantially transparent, water insoluble, chemically setting plastic into a shaped mold. While in the liquid state, items of the following types are embedded: mummified tissue from a deceased or living biological subject, an epitaph, memorabilia, and a label describing the biological content and purpose of the tissue. The four types of embedded items enclosed together in a single object accord with the definition of a tomb. Mummified tissue protected from water, air, illumination, and bacterial action preserve the genome of the subject and provide a potential for resurrection of a biological subject by anticipating future innovation in genetic engineering and somatic cell cloning. Portable tombs may be prepared ante mortem as well as post mortem. Multiple equivalent tombs may be made for one individual. Multiple individuals may be entombed in a single portable object. A portable tomb consumes no land, makes visitation travel unnecessary, and may multiply entomb a single individual, or singly entomb multiple individuals.

11 Claims, 1 Drawing Sheet

PORTABLE TOMB FOR RESURRECTION FROM MUMMIFIED TISSUE DNA

BACKGROUND OF THE INVENTION

1. Field of the Invention

The present invention relates to a portable tomb containing: mummified tissue with DNA of a deceased in expectation of future resurrection, an epitaph, various memorabilia, and a label; all memorializing the dead.

2. Description of Prior Art

The conceptual prototype of a tomb is the Egyptian pyramid. A pyramid is a large above ground historical structure which contains: mummified remains of a deceased in a sarcophagus; epitaphs identifying and memorializing the dead; memorabilia (objects of value) pertaining to the life history of the deceased; and objects and information pertaining to the continuation of life in some form. Pyramids are singular, large, and immobile. The present invention corrects all these features.

Throughout recorded history, humans have established graves or mausoleums to entomb remains of a deceased. The tomb is marked with an epitaph on a tombstone identifying the deceased. In most cultures grave markers and tombstones are used to memorialize the deceased. Usually relics from the deceased's life are entombed. Implicitly such practice reflects a belief in an afterlife or resurrection of the dead. The permanence of tombs and grave markers addresses and comforts the family by permanence of the structure symbolizing an everlasting life. It confirms feeling for the continuity of life. In Christian liturgy the "dead shall rise from the grave, and the sea shall give up its dead" confirms the idea of physical resurrection from remains.

Corpses are bulky. Disposition of the dead by burial is customary presumably in the interest of sanitation. Burial sites are immobile. Increasing cost of preservation, decreasing availability of burial land, and population mobility exert new pressures on burial practice. Systematic reduction of burial mass has evolved.

Most commonly, cremation and preservation of only part of the deceased has gained in popularity. The resultant reduction in size of mortal remains is farther augmented by burial at sea, or scattering in sentimental sites, on public or private land. Although long and widely practiced the entire prior art pertaining to cremation is not relevant to the purposes of the portable tomb. In cremation the mineral remains cannot be biologically identified with the deceased person. Contemporary scientific belief is that the complete and unique biological specification of an individual is embodied in cellular DNA, principally as the genome. In consequence, only this portion is sufficient for biological resurrection. The concept of resurrection becomes anomalous. Systematic preservation of the cytological and genetic components avoids this anomaly to preserve biological identity.

Reduction of mass has been accomplished by preserving only part of the body. Preservation of partial mortal remains has been practised in various forms by different cultures as in head hunting, scalping, collecting ears, locks of hair. In non-human species taxidermy is the practice of preserving hides, heads, and other portions of a deceased. Tissue from a deceased has been preserved post mortem for non-memorial purpose: in paraffined tissue blocks used for autopsy and histopathology purposes, museum specimens, historical pickled brain collections, Galileo's dried finger, and John Dalton's eyes. Many of these practices involve drying. The remains are kept in ordinary environments. In some instances such tissue specimens have been analysed for genetic (DNA) sequences unique to the deceased. In no instance was preservation of a deceased intended to address the possibility that biological resurrection may be accomplished through future techniques in somatic cell cloning. Appropriate genetic engineering technology will most certainly evolve in the next milennium.

The reduction of mass in cremation permits funerary urns and cremation caskets, to be less than one cubic foot in size. U.S. Pat. No. 5,287,603 Schorman describes a box sized plastic container, and in U.S. Pat. No. 5,379,499 Jackson a specially shaped urn with a second compartment for memorabilia or flowers. These were intended to be interred in graves with customary, bulky grave markers. Many ash containers are placed in columbaria above ground also of monument size and form. In U.S. Pat. No. 4,739,595 Yamagata proposes a building sized electronically controlled display of multiple urns and associated religious and identifying information to be called up electronically during religious visitation. While such use is individualized and more mobile than outdoor columbaria the installation does not capitalize on portablility and remains are mineralized. Animal cinerary urns are sometimes kept in the home. U.S. Pat. No. 5,158,174 Hereford describes an extreme reduction in storage volume of ashes in a design of a jewelry container to be worn as a kind of amulet. In Asia, urns are commonly kept in special sites in the household or in temples. While cremating reduces the mass of the deceased remains permitting portability, biological identity is lost. An alternative to cremation is mummification in which water and other volatiles constituting about 70 percent of the body mass are removed. Protected from water such remains remain recognizable for centuries. Mummification processes occur in nature in the high desert and in arid regions. Techniques like those of Egypt and Inca are not well documented to serve as prior art. Analysable and unique DNA suitable for study of evolutionary genetics of insect species have been recovered from paleolithic amber. Dessication by various methods is the basic process for preserving tissue for study in molecular biology and genetics. In funerary practice U.S. Pat. No. 397,379 Meyers dries a corpse by sealing the casket and pumping dry air through it. Improved dessication by including chemical desiccants in the coffin is proposed in U.S. Pat. Nos. 1,252,090 Clayton, and 1,120,336 Schnee and Riley. Mummification before interment is described in U.S. Pat. No. 1,088,977 Fratarcangeli in which the corpse is immersed in alcohol and turpentine followed by sun drying. Dry chemical desiccants used are calcium oxide in U.S. Pat. No. 1,120,336, and anhydrous calcium sulfate in U.S. Pat. No. 1,252,090. All these methods deal with the entire corpse perhaps with viscera removed. There is reduction in weight but not greatly in size because of the skeletal structure. The present invention however combines preservation of biological uniqueness of the deceased and a potential for resurrection by storing an antiseptically dried sample of whole nucleated cells containing both nuclear and cytoplasmic DNA as well as other components related to the genetic identity of the deceased. This is accomplished in a sample of small weight of gram or milligram size. Multiple aliquots of tissue from a single subject may be prepared and stored separately. The proposed method for preserving the dead rests upon contemporary understanding of the significance and form of the genetic DNA code.

Preservation by cryogenic (freezing) is proposed. In U.S. Pat. No. 3,408,712 Pauliukonis describes freezing the whole corpse in liquid nitrogen and preserving it intact in the frozen state. U.S. Pat. No. 4,067,091 Backman, describes freezing remains in liquid nitrogen and crushing the remains while in the frozen state followed by drying. There is significant reduction in mass. Freeze drying relates to expectation of unspecified future scientific advances. Cryogenic establishments are immobile, few, and expensive.

Preservation of remains for museum and funerary practice resemble laboratory formulation in clinical microscopy. These chemical treatments are intended to prevent decay and preserve cytological detail. U.S. Pat. Nos.: 2,106,261 Weidmann, 5,350,670 Yeh, and 5,405,606, 5,607,668, and 5,662,695 Campbell are typical formulations under patent. These propose advantages in preserving appearance of the deceased, better infiltration, research utility or safety for mortuary workers. The formulations are generally bactericidal and precipitate tissue protein.

U.S. Pat. No. 748,284 Karwowski describes a method for preserving the dead by embedding the fully clothed corpse or head in a solid block of glass. Said object is available for display and not entombed. Since it was patented in 1903 it can have no relevance to the problem of resurrection through DNA or somatic cell cloning, nor does it reduce mass or increase portability.

Physical association and preservation of mementoes of the social being are the usual addition to remains in burial practice. As in the case of the pyramid, these account for most of the immobility of tombs. Grave markers generally document and preserve information about the social position, religion, and environment of the deceased. The grave marker art addresses cost, appearance, permanence, lighting, and maintenance. In the context of a portable tomb there is little in prior art that is relevant except as they refer to physical materials used, or kind of memorabilia contained in the grave marker. Representative innovations include:

U.S. Pat. No. 4,304,076 to Splendora discloses a grave marker molded from transparent plastic material, specifically methyl-metacrylate. Personal or written items are to be embedded in the material. The plastic may be formed into three dimensional shapes indicative of significant aspects of the decedent's life. U.S. Pat. No. 5,014,472 to Svenssen discloses a material for lighter weight fixed grave marker to replace wood in longevity. U.S. Pat. No. 4,058,940 to McBrayer discloses a monument marker formed with a clear plastic outer laminate and an inner concrete core. Its significance lies primarily in the use of plastic to increase durabilty of the marker and protects markers from vandalism and removal. The three patents refer to gravemarkers affixed to the gravesite. Reference to weight of marker material is not directed at portability.

In addition to the usual epitaph a wider class of memorabilia is associated with the gravemarker in several U.S. Patents. U.S. Pat. No. 4,377,109 to Narita discloses a plastic ornament which is fixed to tombstone or burial monument. The ornament is transparent and is sealed to the monument to protect a photograph, document, or other memento of the deceased. Both Narita and Splendora through use of plastic make mementoes accessible for the benefit of visitation. Their procedure affixes memorabilia to grave marker to make them accessible at visitation. Their disclosures do not alter the fixed site property of the tomb. U.S. Pat. No. 5,564,816 to Arcadia discloses an illuminated and rechargeable light source in a grave marker to light fixed grave markers and local graveyard area at night. U.S. Pat. No. 5,225,170 to Plamp discloses another illuminated memorial. The Plamp memorial provides illuminated grave markers with photovoltaic power to recharge batteries for the light power. Thus Plamp extends Arcadia. Both Arcadia and Plamp provide site illumination for visitation use. Such illumination is not pertinent to portability or memorabilia of the deceased.

Several patents disclose extension of grave marker construction to include electrically powered devices to include non-visual memorabilia. U.S. Pat. No. 5,404,343 to Boggio discloses and claim an audio system within a marker such as a gravestone or tombstone. The Boggio audio system uses photovoltaic power and semiconductor electronics to recover digitally stored audio information. The addition of an electronically active memento simply extends the definition of funerary objects comprising contents of a tomb to contemporary technology. As described it adds to the mass of a fixed grave marker. These inventions simply extend the class of memorabilia to include electronic devices and do not imply or specify either portability or resurrection potential.

Patented modification of traditional grave markers do not address the modern problems of shortage of graveyard space, the requirement for a fixed location. Use of lighter materials were undertaken to prevent vandalism, increase durability, improve visitation, and visualization of memorabilia.

SUMMARY OF THE INVENTION

It is an object of the present invention to preserve and memorialize the dead in a portable and durable object. The memorial objects are small, portable, solid castings in which are embedded chemically fixed, dried, tissue; tissue DNA; an epitaph; a content label; and memorabilia of a deceased. The tissue and DNA of the person collected antemortem or postmortem is sealed into a small metal container (sarcophagus) before embedding in the clear plastic. Memorabilia may consist of photographs, writing, art objects, electronic devices, medals, jewelry, or other small items prized by the deceased. A written or engraved epitaph commemorating the life of the individual make up the remainder of a tablet. Electronically stored sound (voice) or pictorial messages are stored on the electronic devices included. In several millennia DNA may be recovered and an organism resurrected as in the fantasy portrayed in a motion picture. A written content label is included to indicate the potential for such future use. The matrix and contents are expected to endure several hundreds of years without special environmental protection and without interment. The object provides a possibility that future technology may make possible the creation of a physical individual with a genome that corresponds to the person whose DNA is embedded. By interring the whole or major portion of the remains there may be but one tomb. In contemporary mobile society, family and friends may be widely separated from each other and the gravesite. It is often difficult for family members to visit a distant site. By preserving a genetically complete aliquot in each portable tomb, multiple tombs for geographically separate sites may be prepared. Such tombs will differ in respect to choice of stored memorabilia but each contains a complete unique copy of the deceased's genome. Tombs are made by embedding all components in a portable mass of water insoluble, durable, clear material. Cells and relevant DNA may be collected ante-mortem and from a deceased in situations where trauma makes available only part of a body. More than one sarcophagus may be embedded in one casting with appropriate identifying information permitting burial of spouses or other related persons. One tomb of portable size may be revised by casting new material in a somewhat larger mold along with an existing one. Through use of plastic casting the present invention provides an improved means for memorializing the dead with a potential for physical resurrection by some future extension of somatic cell cloning.

Figure 1:
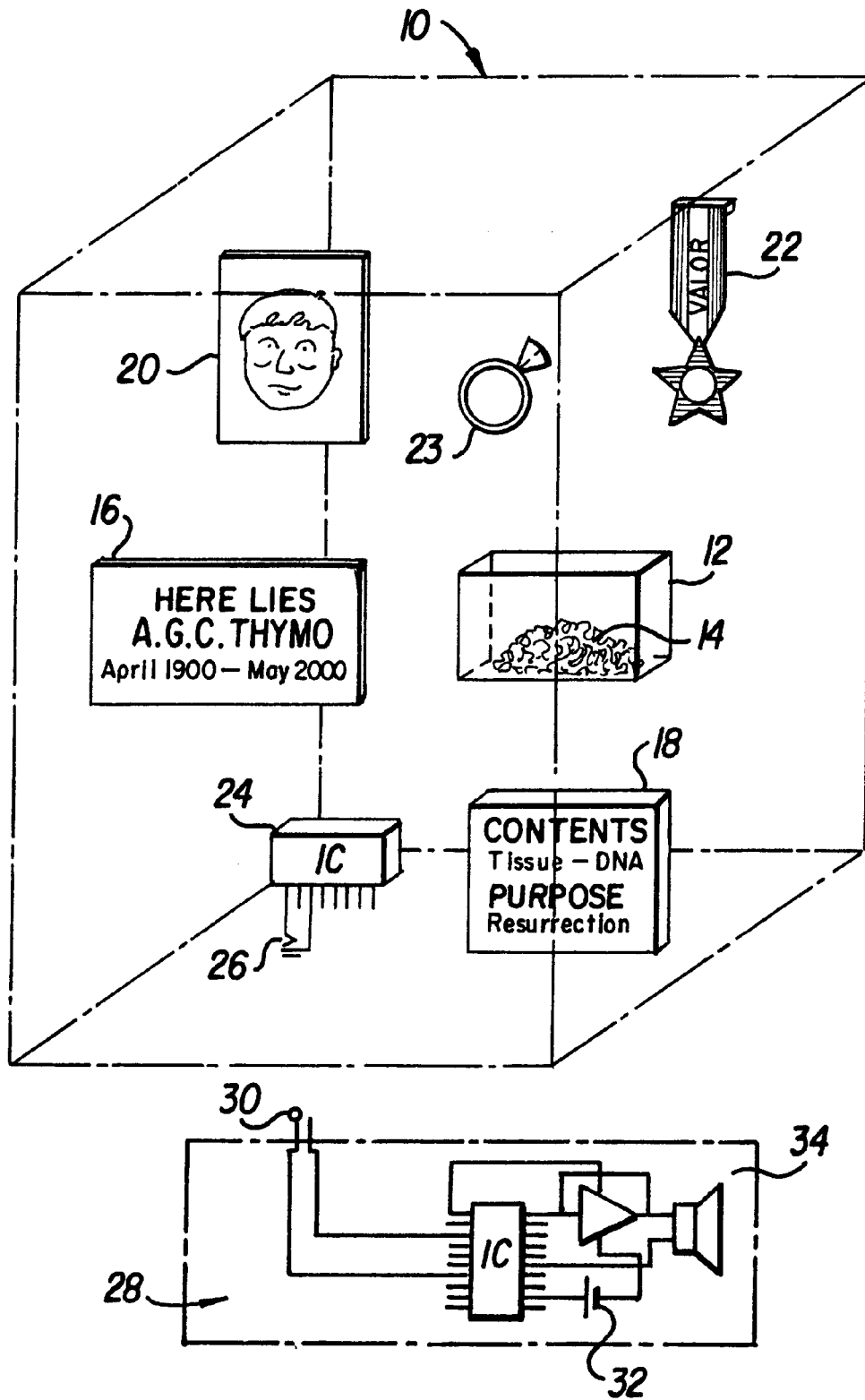
FIG. 1 of 1

| NUMBER | PART NAME |
|---|---|
| 10 | cast plastic solid |
| 12 | metal box sarcophagus |
| 14 | mummified tissue DNA and adjuvants |
| 16 | epitaph |
| 18 | content label |
| 20 | memento - a picture |
| 22 | memento - a medal |
| 23 | memento - jewelry, a ring |
| 24 | memento-electronic memory |
| 26 | electronic connector to surface |
| 28 | illustrative external support assembly |
| 30 | illustrative electronic connector -mating connector 26 |
| 32 | illustrative external power source |
| 34 | illustrative enabling electronics for electronic memento 24 |

DETAILED DESCRIPTION OF THE PREFERRED EMBODIMENT

A typical embodiment of the invention is illustrated in FIG. 1. The tomb 10 is of portable size, and composed of a clear, water insoluble, thermally stable, plastic like acrylic, polystyrene, or epoxy. The plastic obtained in liquid form is mixed with a suitable catalyst at room temperature. The mixture is cast into a mold suitably shaped to geometric, artistic, or sacred form. At the instance of casting, fixed dried tissue 14 constituting the DNA sample of the individual, a sarcophagus (container) 12, a written epitaph 16, a content label 18, and mementoes 20 22 23 24 are suitably embedded. The resulting object 10 constitutes no health hazard and is suitable for placement in a household. It does not require interment in a burial plot.

DNA 14 is taken post mortem by tissue biopsy. Samples may be from any body tissue. The preferred tissues are: skin (dermis), connective tissue, marrow, blood, spleen, lymphnode, testes, ovary, or liver which contain cells capable of regeneration. These tissues are not characteristically host to bacteria. Cells collected post mortem may be dead or even partially autolyzed but not putrefied. Antemortem, tissue samples may be collected as blood, semen, or by biopsy. In each case, the unique genome of the individual is preserved. These tissue preferences are intended to avoid the use of terminal cell lines like brain or muscle. Using whole tissue preserves cytosomal components of the cells whose role in defining the individual are not clear at this time. The problem of contamination with bacterial and viral DNA is reduced to some extent by using deep tissues and aseptic technique for sampling. Sterilization by chemical fixation does not eliminate the possibility for contamination by bacterial DNA, but minimizes it through relative sample size and tissue choice.

Tissue blocks or fragment 14 not less than one gram in weight or blood samples at least 10 ml. in volume are preferred. Blood should be collected preferably in a plastic tube containing an anticoagulant like EDTA. Before fixation, blood should be divided to remove the red cells whose hemoglobin is known at present to interfere with DNA chemistry. Such separation may be accomplished using modern cytological laboratory technique like concurrent hemolysis and centrifugation. More simply, hemoglobin content is sufficiently reduced by sedimenting clot inhibited blood at 1 G. in a tube standing in a household refrigerator and decanting all the supernatant plasma, the buffy coat, and the topmost layers of sedimented red cells. Semen may be collected using procedures for artificial insemination into a clean glass or plastic container.

PRESERVATION: All samples are fixed and dried while refrigerated before sealing in a sarcophagus 12.

FIXATION: It is currently believed that the best method for preserving tissue in a chemically pristine state is freeze drying. Tissue is placed in liquid isopentane in liquid nitrogen at −160 deg C. and dried in special drying devices which evacuate the volatile components. In usual histo-pathology procedure this is followed by embedding.

While such a procedure may be followed, simpler and commonly used fixatives or embalming fluids may be used at much lower cost. There are many formulations in standard manuals for histo-pathology laboratory practice. The following recommendations will help select those to be preferred. Avoid fixatives which contain metal ions like chromium, osmium, lead, or mercury specified in some histo-pathology formulations. Acetone, alcohols (ethanol, methanol, propanol), formaldehyde-alcohol mixtures, buffered formaldehyde, or acetic-formaldehyde-alcohol fixatives which are wholly volatile and leave little residue are preferred. The volume of fixative solution for blood and semen should at least equal the sample volume. For other tissues a relative volume of 5 to 20 of fixative to tissue should be observed. The usual disadvantages reported with many of these fixatives such as hardening are not a disadvantage in the present application. Autopsy samples are likely to be contaminated even if plausible precautions are taken to use clean instruments. Prompt fixation and chilling should minimize the effects of bacterial growth. Any medical laboratory text will contain formulations for fixatives suitable for use. A typical reference for details is Lynch's Medical Laboratory Technology 3rd ed. 1976, Ed. S. Raphael, W. B. Saunders and Co. Philadelphia, Pa. Vol 2 pp. 876–888. ISN 0721674631.

DRYING AND PACKING

The fixed tissue 14 is placed in a flat open container placed in a desiccator (covered airtight jar) over any commonly available laboratory dessicant; e.g. calcium chloride, silica gel, magnesium perchlorate (all sold under various commercial tradenames). The entire desiccator is refrigerated until tissue is dried. Five to ten days at temperatures attainable in an ordinary household freezer removes all perceptible moisture and volatile components of the fixative. The dried product 14 preserves DNA and all non-volatile tissue components present in the original sample. Bacteria present should have been killed. DNA and tissue components are preserved chemically to minimize racemization and decay. Using a sterile mortar and pestle the tissue fragments may be reduced to a powder or left if the particle size is compatible with packing in the metal container (sarcophagus) 12.

The resultant powder 14 is sealed in a small metal box, tube, or shaped container (sarcophagus) 12. The metal may be common or noble. The dried product is transferred to the sarcophagus with or without adding substances 14 to exclude air. Preferred air displacing material are those not requiring heating e.g. cedarwood oil, silicone, or mineral oil. Other substances such as silica gel, antioxidants like ascorbic acid, citric acid, or cellulosic embedding material may be included to fill any large voids in the sarcophagus 12. Air displacing material to fill voids serve to maintain the sample in a dry state and diminish possible oxidative deterioration by residual oxygen. The metal sarcophagus 12 protects the DNA material from illumination and to a lesser extent from radiation. Removal for resurrection will be simplified if embedding plastic does not infiltrate the tissue, or over time react with the dried tissue.

EMBEDDING Techniques for plastic embedding of objects are well developed in the medical, museum, novelty, and trophy industries and no new technology is required. Collectively the techniques involved are common within the scope of the hobby, craft and home workshop arts such that the manufacture of portable tombs by individuals from kit form is practical and intended. Materials, suitable kits, and instructive publications can be obtained from Castolite Co.; P.O. Box 391; Woodstock, Ill., 60098, and ETI Resin Craft Products, Fields Landing, Calif. 95537, and Carolina Biological Supply Co., 2700 York Road, Burlington N.C. 2721-3398. Suitable publications for casting methods may be obtained through model making magazines, or from CASTCRAFT, Box 17000, Memphis, Tenn. 38187-0080. CASTCRAFT also sells a listing of source materials and advice for commercial production of plastic castings. These are art methods for the hobbyist and do not require industrial machines or methods. Scientific and custom casting of biological specimens may be obtained from Carolina Biological Supply Co., 2700 York Road, Burlington, N.C. 27215.

The sarcophagus 12 is embedded in plastic by casting and polymerization using a non-thermal plastic like epoxy, polystyrene, or acrylic. These plastics are purchased in two components: a liquid and a catalyst for polymerization. The two ingredients are mixed in manufacturer specified proportion and poured into a suitably shaped mold. The mold may be a glass or metal container of selected size; or one made from wood to a desired shape and sealed against adhesion of plastic, or one of the commercially available adjustable mold forms. Application of releasing compound or vaseline grease on the mold before casting is advised to simplify release of the tomb 10 from the mold. These plastics do not require heating to solidify. The plastic mix is poured in layers and the embedded items may be placed at the selected level in the final solid. During casting the mold and contents should be protected from dust and kept still to permit any bubbles to escape before the plastic becomes firm. The mold with setting plastic may be held under positive air pressure to expedite bubble removal but this is not ordinarily necessary. After setting, the tomb is removed from the mold and shaped to remove rough edges or deformities and polished to provide a clear image of the contents. Access to any electrical connectors 26 to devices 24 embedded as memorabilia is opened. Further investment of the casting in glass or non-plastic container increases the longevity of the tissue DNA 14 but diminishes potential for revision or viewing.

A typical embodiment is a hand held block approximately 12 cm×6 cm×3 cm. An embedded metal sarcophagus is sized to contain not less than 300 mgm of dried tissue about 0.5 ml. Adjuvant will increase the size of the sarcophagus 12. Mementoes are small objects like a medal 22, wedding ring or jewelry 23, photographs 20. Another class of memorabilia includes encapsulated integrated solid state circuits IC devices 24 to provide illumination of the visual images, or means for sound reproduction of the deceased's voice, or a digitized image. Tombs that speak or react result. Solid state devices IC 24 require power and implementing electronics.

Active memorabilia may be solar or externally powered. Externally powered devices require means for electrical supply connection. Means for such connection 26 are exposed to the surface of the object 10 are embedded.

Externally powered tombs will require associated electronic circuits to recover stored information. Said circuitry is shown diagrammatically 28 as separate from and not integral to the portable tomb 10 in FIG. 1. Said diagram is not a working circuit and shows an optional object 28 containing as principal components: a means for power 32, activating electronic circuits 34, and connectors 30 to mate with connectors 26 on the tomb. The base and numbered parts 28 30 32 34 shown in FIG. 1 are shown for completeness of the description and are not intended as component to the portable tomb disclosed in previous paragraphs.

The epitaph 16 and content label 18 are printed. Said printing may be accomplished by print on paper, engraving or etching metal, or as a drawing, photograph, a phototransparency. The wording on the epitaph 16 is information in style common on tombstones such as the name, birth date, passing date, and sacred sentiment. The content label indicates presence of mummified DNA 14 in the sarcophagus 12 and purpose for resurrection. The word resurrection is used to denote an at present imagined process by which an individual bearing the genome of a deceased may be constructed into a living organism from cell residue; and, literally be born again. The biotechnology involved seems certainly to evolve from contemporary methods for study and replication of DNA and somatic cell cloning of plants and animals. As in the Christian text this implies no resurrection of the social being or experienced sin to be part of the reborn organism.

Tomb 10 prepared antemortem may be updated after death by surface engraving, or by making a cavity in the solid plastic and casting new plastic in said cavity along with new items such as a written date of death. Additions to the tomb 10 may also be made by embedding the entire object and new items in a larger one. An addition may contain items to update the deceased's curriculum vitae. Two tombs 10 may be adjoined by embedding both in a common larger casting. Such an embodiment provides the possibility for spouses to be adjoined. Other pairing is possible such as parent and child, close friends, or even small groups of persons.

An embodiment may be a tomb 10 sufficiently small to be worn as a medallion and fitted with a chain or clasp for personal adornment. The shape may be of religious, cultural or, historical significance; or take natural form like animals or plants. A cylindrical casting may be used to augment conventional or existing tombstones by boring monuments to receive said cylindrical casting containing tissue DNA 14 and sarcophagus 12. An embodiment for a tomb 10 may be of a size suitable to be embedded in an item of memorabilia like the frame of a portrait or a commemorative plaque. In this instance the sarcophagus 12 and mummified DNA 14 are embedded and fixed permanently in the item of memorabilia. The object 10 invented is a complete tomb, portable, not requiring special storage facilities, and capable of multiple embodiment. For one deceased, multiple tombs 10 may be constructed before or after death and be distributed to multiple family members.

It is not possible to estimate the longevity of the DNA in the epitaphs. The longevity of insect DNA in specimens extracted from paleolithic amber has been estimated at seventeen million years (Science 272:810,1996). Considering estimates on the recemization of amino acids, one may conservatively estimate 10,000 years as the expectancy of the dried tissue. With reasonable care, a plastic embedded metal sarcophagus 12 most certainly will survive for centuries.

I claim:

1. A method of preserving a DNA specimen of a biological subject and commemorating the biological subject, the method comprising:

embedding memorabilia of said biological subject in a substantially transparent, water insoluble, material;

selecting a body part of said biological subject as suitable for providing said DNA specimen;

removing and preserving a portion of said body part to form said DNA specimen such that said DNA specimen substantially preserves a genome of said biological subject;

encapsulating said DNA specimen in a container, said container protecting said DNA specimen from radiation;

embedding said container in said substantially transparent, water insoluble material; and labeling said substantially transparent, water insoluble material with an identification for said biological subject and with information that identifies said DNA specimen in said embedded container so as to form a portable tomb for said biological subject.

2. The method of claim 1 further comprising:

embedding a solid state circuit in said substantially transparent water insoluble material, said solid state circuit for receiving and storing a digital message that relates to said biological subject.

3. The method of claim 1 further comprising:

adapting said substantially transparent material for convenient transportation by reducing the size and weight of said substantially transparent material for physical transportation by a single human hand.

4. The method of claim 1 further comprising:

embedding a display device substantially into said substantially transparent material, said display device operationally connected to a solid state circuit wherein said display device displays images from information recorded in said solid state circuit.

5. The method of claim 1 further comprising:

adapting said substantially transparent material for convenient use by reducing the size and weight of said substantially transparent material and adapting the shape of said substantially transparent material for use as jewelry.

6. The method of claim 1, wherein said container is formed of metal.

7. The method of claim 1, further comprising:

forming a plurality of said portable tombs for said biological subject; and transporting said plurality of said portable tombs to geographically separate sites.

8. The method of claim 1, wherein said portion of said body part is removed ante mortem.

9. The method of claim 1, wherein said portion of said body part is removed post mortem.

10. The method of claim 1, further comprising:

forming a second said portable tomb for a different said biological subject; and affixing the portable tomb and the second portable tomb together.

11. The method of claim 1, further comprising transporting said portable tomb by hand to a location independent of any place of interment of a remainder of said biological subject.

* * * * *